(12) United States Patent
Millar

(10) Patent No.: US 7,803,381 B2
(45) Date of Patent: Sep. 28, 2010

(54) RETRO-INVERSO GONADOTROPIN-RELEASING HORMONE PEPTIDE AND VACCINE COMPOSITION

(75) Inventor: Robert Peter Millar, North Berwick (GB)

(73) Assignee: Shimoda Biotech (Pty) Ltd., Port Elizabeth (ZA)

( * ) Notice: Subject to any disclaimer, the term of this patent is extended or adjusted under 35 U.S.C. 154(b) by 1015 days.

(21) Appl. No.: 10/534,282

(22) PCT Filed: Nov. 7, 2003

(86) PCT No.: PCT/IB03/05008

§ 371 (c)(1),
(2), (4) Date: Apr. 10, 2006

(87) PCT Pub. No.: WO2004/043994

PCT Pub. Date: May 27, 2004

(65) Prior Publication Data

US 2009/0136527 A1    May 28, 2009

(30) Foreign Application Priority Data

Nov. 9, 2002    (GB)    .................. 0226179.0

(51) Int. Cl.
*A61K 39/00*    (2006.01)
*A61K 38/08*    (2006.01)
*A61K 38/09*    (2006.01)
*A61K 38/10*    (2006.01)
*C07K 7/00*    (2006.01)

(52) U.S. Cl. ................. 424/185.1; 424/193.1; 530/327; 530/328; 514/15

(58) Field of Classification Search ........................ None
See application file for complete search history.

(56) References Cited

U.S. PATENT DOCUMENTS 5,434,136 A *   7/1995   Mathias ........................ 514/15

7,361,349 B2 *   4/2008   Meloen et al. ........... 424/185.1

FOREIGN PATENT DOCUMENTS

WO    WO 92/12247    7/1992

OTHER PUBLICATIONS

M. Hervé et al. Mol. Immunol. (1997) 34(2), pp. 157-163.*
N. Chaturvedi, et al., "*Topochemically Related Hormone Structures*", Int. J. Peptide Protein Res. 17, (1981), pp. 72-88.
N.J.C.M. Beekman, et al., XP-002282907, "*Highly immunogenic and fully synthetic peptide-carrier constructs targeting GnRH*", Vaccine 17, (1999), pp. 2043-2050.
L. A. Miller, et al., "*Immunocontraception of White-Tailed Deer with GnRH Vaccine*", American Journal of Reproductive Immunology, vol. 44, (2000), pp. 266-274.
International Preliminary Examination Report dated Mar. 29, 2005.

* cited by examiner

*Primary Examiner*—Robert B Mondesi
*Assistant Examiner*—Padma V Baskar
(74) *Attorney, Agent, or Firm*—Morrison & Foerster LLP

(57) ABSTRACT

The invention describes a retro-inverso (RI) gonadotropin-releasing hormone (GnRH) peptide which is capable of eliciting an immune response directed against GnRH, the peptide having the amino acid sequence GPRLGYSWHX, wherein the amino acids are D-amino acids and X is any amino acid. More particularly, X is E, Q, P or G, and even more particularly, X is E or Q. Thus, a preferred amino acid sequence for the peptide is GPRLGYSWHE. The peptide may optionally include one or more additional D-amino acids at its N- or C-terminus, for example a cysteine residue or a series of linker amino acids, such as a plurality of glycine amino acid residues. Thus, a second preferred amino acid sequence for the peptide is GPRLGYSWHEC, which includes a cysteine residue at the C-terminus for conjugation purposes. The invention also describes a vaccine composition for use in controlling fertility, heat, contraception and/or treating sex hormone-related diseases, and a method for controlling and or treating fertility and sex hormone-related diseases.

18 Claims, 11 Drawing Sheets

RETRO-INVERSO GONADOTROPIN-RELEASING HORMONE PEPTIDE AND VACCINE COMPOSITION

BACKGROUND OF THE INVENTION

The invention relates to a retro-inverso gonadotropin-releasing hormone (RI-GnRH) peptide and the use thereof as a vaccine.

The decapeptide gonadotropin releasing hormone (GnRH) regulates the reproductive hormone cascade by stimulating the release of gonadotropins from the anterior pituitary, which in turn regulates reproductive function. GnRH is synthesised in the neurones of the hypothalamus and released into the portal circulation where it interacts with GnRH receptors on the gonadotrope cells in the anterior pituitary [6]. Stimulation of the GnRH receptor is essential for the secretion of luteinizing hormone (LH) and follicle stimulating hormone (FSH), which in turn are required for steroidogenesis and gametogenesis, respectively [6]. Due to this central role in reproduction, GnRH peptide analogs have found therapeutic applications in controlling fertility, cryptorchidism, polycystic ovarian syndrome, leiomyomata, endometriosis, acute intermittent porphyria, and breast, ovarian and prostatic cancer [3, 16].

It has been reported that up to 80% of female cattle sent to abattoirs are pregnant. As some of the feed ingested by pregnant cattle is diverted to the unborn calves, especially during the last three months of gestation, there is a loss of body tissue in adult female cattle and thus less beef is obtained from these cattle. This results in a loss of value of the pregnant animal.

Recognition of the importance of avoiding pregnancy in female cattle which are destined for slaughter has led to various methods to avoid fertility, such as surgical spaying. This is an unpleasant procedure with several side effects, and additionally, permanent sterilisation is not always desirable. For example, in the beef and dairy industry, pregnancy too soon after calving is a major problem, and it would be desirable to induce a temporary state of infertility in these cattle to allow them to recover after calving.

There is also a need for controlling gonadal activity in other domestic animals and wild animals, and in chronic diseases in humans.

Peptide-based vaccines which can be administered to cattle by way of injection to reduce their fertility are known [1, 17]. These vaccines against L-amino acid native GnRH conjugates stimulate the animals' immune systems to produce antibodies that block the hormonal pathway involved in reproduction. The vaccines have subsequently also undergone clinical trials in treatment of prostate cancer in humans [22] and have potential in sex hormone-dependent male and female cancers [8, 21]. Antibodies to GnRH have also been raised in a number of species by chemical conjugation of GnRH to a suitable carrier and administration of the conjugate in an appropriate adjuvant. Recombinant fusion proteins comprising GnRH or GnRH-analogues have also been described for use in peptide vaccines for the immunological castration or inhibition of reproductive function of various domesticated and farm animals.

The advantages of peptide based vaccines are well described as they are chemically defined, are indefinitely stable and can be stored as a freeze dried powder. The preparation does not require large-scale production and is relatively cheap. However, a major limitation of peptide vaccines is their relatively low immunogenicity and limited biological half-life [20]. In this regard, prior GnRH constructs have failed to provide a uniformly successful immunological sterilization vaccine product due to the fact that GnRH is a small "self" molecule that is not normally recognized by a subject's immune system, rendering the molecule poorly immunogenic and inherently unable to induce a significant immune response against endogenous GnRH. Chemical conjugation protocols are also difficult to control, rendering substantially heterogenous and poorly-defined GnRH conjugates. The peptide nature of GnRH vaccines has necessitated administration by means of injection along with adjuvant.

An alternative approach to immunization with native peptides is the use of peptidomimetics such as retro-inverso (RI) peptides that could serve as vaccines. RI peptides which produce antibodies directed against large polypeptides of foot and mouth disease virus are known. Antibodies to these RI peptides have been reported to show greater affinity than antibodies to classical L peptides and show strong neutralizing activity. However, RI peptides which are directed to small biologically active peptides such as GnRH have not been reported. As the N and C termini (pGlu and Gly-NH$_2$), which are important for binding of GnRH to its cognate receptor, cannot be simulated in RI-GnRH [NH$_2$—CH (C$_2$H$_4$COOH)—CO— and NH$_2$—CH—CO—], and because of the many differences between small peptides and large polypeptides, it is not predictable that antibodies raised against RI-GnRH would immunoneutralise the native peptide.

Thus, although a variety of contraceptive methods are available to control fertility, each has disadvantages such as affordability, application difficulty (injections), daily intake (pills) and irreversible procedures (surgical methods).

There is therefore a demand for an improved and a cost-effective approach to regulate reproductive function and sex hormone-related diseases. The development of a potent immunogenic active GnRH vaccine would therefore greatly enhance the utility of this pharmaceutic agent in current therapies.

SUMMARY OF THE INVENTION

According to a first embodiment of the invention, there is provided a peptide having the amino acid sequence GPRLGYSWHX, wherein the amino acids are D-amino acids and X is any amino acid (SEQ ID NO:3). More particularly, X is E, Q, P or G (SEQ ID NO:4), and even more particularly, X is E or Q (SEQ ID NO:5). Thus, a preferred amino acid sequence for the peptide is GPRLGYSWHE (SEQ ID NO:1).

The peptide may optionally include one or more additional D-amino acids at its N- or C-terminus, for example a cysteine residue or a series of linker amino acids, such as a plurality of glycine amino acid residues. Thus, a second preferred amino acid sequence for the peptide is GPRLGYSWHEC (SEQ ID NO:2).

According to a second embodiment of the invention, there is provided a vaccine composition capable of eliciting an immunological response in an animal to which it is administered, the composition comprising:

(a) an immunogenic peptide substantially as described above; and (b) a pharmaceutically acceptable carrier or excipient.

The peptide may be administered along with or conjugated to a carrier or an adjuvant, or alternatively need not be conjugated to or administered with a carrier or an adjuvant.

If the peptide is administered with or conjugated to an adjuvant, the adjuvant may be selected from CpGs, M59, complete Freund's adjuvant, IFA (incomplete Freund's adjuvant), alum, bile salts, vitamins, attenuated toxins and the like. Examples of attenuated toxins are pertussis or cholera.

The vaccine composition may be used in a method of contraception or a method of controlling fertility and/or heat in an animal.

The animal may be a human. Alternatively, the animal may be a domestic animal, a wild animal, livestock or a fish.

The vaccine composition may also be used in a method of treating a disease in a human. The disease may be a sex hormone-related disease, such as prostatic cancer, breast cancer, ovarian cancer, uterine cancer, endometriosis, uterine fibroids, precocious puberty and so forth.

The vaccine composition may be administered orally, nasally, trans-cutaneously or subcutaneously to the animal. In the case of oral administration of the vaccine, the peptide may be conjugated to a suitable carrier in order to facilitate absorption across the gastro-intestinal tract.

The peptide may be included with or conjugated to another vaccine, in order to reduce the number of injections which are administered to the animal.

According to a third embodiment of the invention, there is provided a method of treating a disease in an animal by administering a peptide substantially as described above to the animal in an amount sufficient to elicit an immune response against GnRH in the animal. The disease may be a sex-hormone-related disease, such as prostatic cancer, breast cancer, ovarian cancer, uterine cancer, endometriosis, uterine fibroids or precocious puberty.

According to a fourth embodiment of the invention, there is provided a method of controlling fertility in an animal by administering a peptide substantially as described above to the animal in an amount sufficient to elicit an immune response against GnRH in the animal.

According to a further embodiment of the invention, there is provided a method of contraception in an animal by administering a peptide substantially as described above to the animal in an amount sufficient to elicit an immune response against GnRH in the animal.

According to yet a further embodiment of the invention, there is provided a method of controlling heat in an animal by administering a peptide substantially as described above to the animal in an amount sufficient to elicit an immune response against GnRH in the animal.

According to yet a further embodiment of the invention, there is provided the use of a peptide substantially as described above in the manufacture of a medicament for use in a method of treating a disease in an animal. The disease may be a sex-hormone-related disease, such as prostatic cancer, breast cancer, ovarian cancer, uterine cancer, endometriosis, uterine fibroids, precocious puberty and so forth.

According to yet a further embodiment of the invention, there is provided the use of a peptide substantially as described above in the manufacture of a medicament for controlling fertility or heat in an animal.

DETAILED DESCRIPTION OF THE INVENTION

Figure 1:
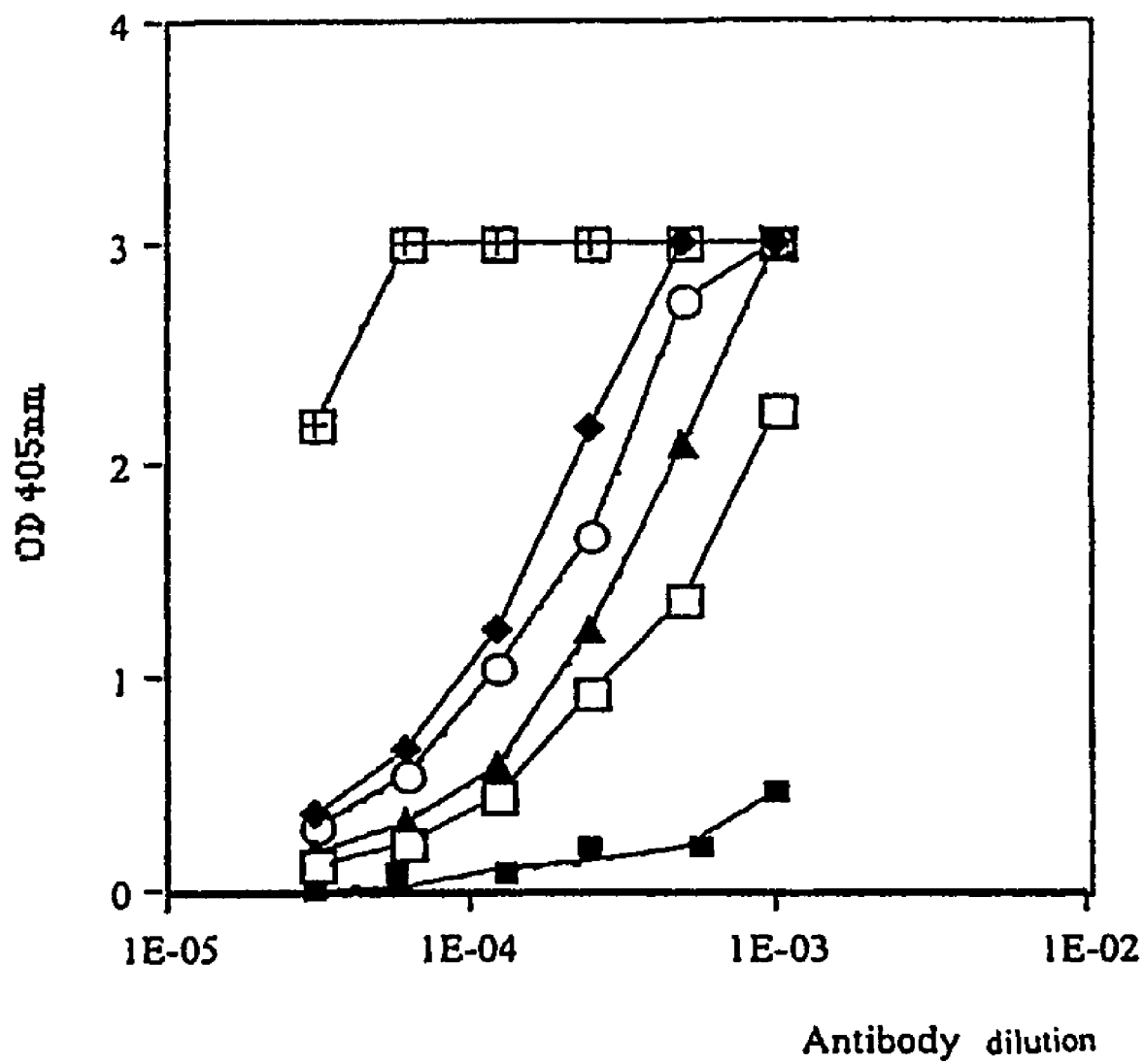
FIG. 1 Titre of affinity with RI-GnRH MOA conjugate of purified fractions of anti-RI-GnRH antibodies from one of the rabbits immunised with RI-GnRH MOA conjugate. The fractions were eluted with KSCN (□), glycine (Δ•), acetic acid-NaCl (○), G-HCl (♦). The binding of whole serum (+) and column flow through (■) are also shown.

The invention describes a retro-inverso gonadotropin-releasing hormone (GnRH) peptide which is capable of eliciting an immune response directed against GnRH, the peptide having the amino acid sequence GPRLGYSWHX, wherein the amino acids are D-amino acids and X is any amino acid (SEQ ID NO:3). More particularly, X is E, Q, P or G (SEQ ID NO:4), and even more particularly, X is E or Q (SEQ ID NO:5). Thus, a preferred amino acid sequence for the peptide is GPRLGYSWHE (SEQ ID NO:1).

The peptide may optionally include one or more additional D-amino acids at its N- or C-terminus, for example a cysteine residue or a series of linker amino acids, such as a plurality of glycine amino acid residues. Thus, a second preferred amino acid sequence for the peptide is GPRLGYSWHEC (SEQ ID NO:2), which includes a cysteine residue at the C-terminus for conjugation purposes.

The invention also describes a vaccine composition for use in controlling fertility, heat, contraception and/or treating sex hormone-related diseases. If the heat cycle in animals is prevented or delayed, controlled breeding of animals will be possible.

Retro-inverso (RI) peptides are peptides where the amino acid residues are aligned in the reverse order of that in the parent peptide and D-amino acids replace the L-amino acids of the parent peptide, making the RI-peptides powerful immunogens [25]. The orientation of the side chains in a RI-analog is very similar to that in the parent peptide, which leads to eliciting antibodies that cross-react strongly with the parent L-structure [2a, 2b, 19].

Developing synthetic vaccines with RI peptides is attractive because it uses stable and chemically defined products with relatively low biological risk and low cost.

In this specification, the term "effective amount" refers to an amount of the peptide which is sufficient to cause a sufficient specific immune response against GnRH when administered to an animal. More particularly, this term refers to the ability of the peptide to cause the production of antibodies able to bind specifically to endogenous GnRH, thus preventing activity of GnRH.

It is also intended that the term "animals" be interpreted to include humans, domestic animals, cattle, livestock, wild animals and fish.

A retro-inverso gonadotropin releasing hormone (RI-GnRH) peptide having an amino acid sequence GPRLGYSWHE (SEQ ID NO:1) according to the standard one letter amino acid code was synthesised using D-amino acids. Another RI-GnRH peptide having the sequence GPRLGYSWHEC (SEQ ID NO:2), i.e. the sequence of SEQ ID NO:1 with a D-cysteine amino acid residue at the C-terminal was also synthesised.

The RI-GnRH peptides may be used either in association with one or more adjuvants or carriers to enhance its efficiency or may be used without being chemically linked or conjugated with an adjuvant or carrier to simplify and reduce the cost of manufacture of the vaccine composition. Suitable adjuvants are CpGs, M59, CFA (complete Freund's adjuvant), IFA (incomplete Fruend's adjuvant), alum, and attenuated toxins (for example pertussis and cholera). The particular adjuvant depends upon the specific species targeted to be treated and the mode of administration chosen.

If the RI-peptide is administered orally, it may be conjugated to suitable agents like bile salts, attenuated toxins and/or activity absorbed vitamins in order to facilitate absorption across the gastrointestinal tract. Nanoparticles composed of inert biodegradable organic polymers may be used to encapsulate the RI-peptides and adjuvants to protect them from gastro-intestinal enzymes and acids, thereby allowing the nanoparticle-peptide complex to reach the M cells and stimulate the B and T-lymphocytes. A killed virus may also be used to encapsulate the peptide.

Additionally, one or more RI peptides may be conjugated to a chemical scaffold, or an RI peptide may be combined with the natural GnRH peptide, by conjugating the natural peptide with a D-cysteine or D-lysine in position 6, or with a free N-terminus or free C-terminus.

A RI-GnRH peptide may be used as a vaccine in animals to elicit an immune response directed against GnRH. The animals may be either male or female animals.

In particular, the vaccine is a contraceptive used in humans, other animals such as companion animals (for example dogs and cats), livestock, wild animals and fish. For instance, the vaccine composition may be administered to genetically modified fish, so that they will not be able to breed in the wild if they escape from captivity. Consequently, they will not contaminate the gene pool of non-genetically modified fish. In addition, administration of the contraceptive vaccine in problem species such as elephants and other invader problem species may allow for greater control of the number of invader species in, for instance, game farms. The contraceptive vaccine will provide a more humane form of sterilization of animals without physical castration in animals.

The vaccine may be administered with, or conjugated to, another vaccine in order to limit the number of vaccines which are administered to an animal. For example, the RI peptide may be combined with one of the dog or cat vaccines which is administered annually.

The vaccine may also be administered to humans to treat sex hormone-dependent diseases such as prostate cancer, breast cancer, ovarian cancer, precocious puberty, endometriosis, uterine fibroids, other sex disorders, steroid sensitive cancers. It may also be used as a contraceptive.

The vaccine may be administered orally, nasally, sub-cutaneously or trans-cutaneously, and the method of administration may depend on the type of animal to which it is administered. Similarly, the dose which is administered will also depend on the animal, and the size of the animal in particular. Thus, a small animal may be administered with from about 1-100 μg peptide, whereas a large animal may be administered with from about 100-10 000 μg peptide. The frequency of administration, which may vary between about 1× and 12×, for example, over a one year period, will also depend on the animal and the nature of the treatment.

The invention will now be described in more detail, by way of non-limiting example, with reference to the accompanying drawings.

Materials

The peroxidase conjugated second antibodies were obtained from Jackson, (Pa., USA) and maleimide activated ovalbumin (MAO) from Pierce Ill., USA. Methylated Bovine Serum Albumin (m-BSA) was obtained from Calbiochem, tissue culture medium from Life Technology (Cergy Pontoise, France), COS-1 cells from ATCC (USA) and myo[2-$^3$H]-inositol was obtained from Amersham (United Kingdom). Chromatography columns and Sepharose beads were from Pharmacia (Uppsala, Sweden). CpG oligonucleotide was synthesised by Eurogenteche (Brussels, Belgium).

GnRH Analogs

Mammalian GnRH [pGlu-His-Trp-Ser-Tyr-Gly-Leu-Arg-Pro-GlyNH$_2$ (GnRH)], chicken GnRH I ([Gln$^8$]GnRH), and GnRH II ([His$^5$, Trp$^7$, Tyr$^8$]GnRH) were prepared by conventional solid phase methodology and purified by preparative C-18 reverse phase HPLC (University of Cape Town)).

Peptide Immunogen

A retro-inverso (RI) peptide corresponding to GnRH (RI-GnRH) was synthesised using Fmoc technology and was purified by HPLC; and its mass was verified by mass spectrometry. The sequence of the RI-GnRH peptide was GPRLGYSWHE (SEQ ID NO:1) (all D-amino acids). A second peptide having the amino acid sequence GPRLGYSWHEC (SEQ ID NO:2) was synthesised to include an additional cysteine residues at the C-terminus for conjugation purposes. This was the peptide which was used in the following examples.

Peptide Conjugation

The day before primary injection, 4 mg RI-GnRH was mixed with 2 mg maleimide-activated ovalbumin (MAO) and incubated for one hour at room temperature. It was then dialysed overnight against PBS (10 mM phosphate, 140 mM NaCl, pH=7.4).

Immunisation

Rabbit Example
Two adult female rabbits (Harlan, Leicestershire, UK) were immunised with RI-GnRH (100 µg/rabbit) conjugated with MAO. The primary injections were given subcutaneously in complete Freund's adjuvant (CFA). These were followed by three booster injections (1 ml/rabbit) in incomplete Freund's adjuvant (IFA) at two week intervals. The last booster injection was given four weeks later using 200 µg free peptide together with 1 mg methylated-BSA (m-BSA). The rabbits were bled one week after each injection. Two experiments were performed with mice to test whether immunization with RI-GnRH would generate GnRH antibodies, and different methods of immunization with RI-GnRH were tested.

First Mice Example (Example 1)
Nine male BALB/c mice (Janvier, France), nine weeks of age, were immunised intraperitoneally (i.p.) with either 25 µg/mouse RI-GnRH conjugated with MAO (n=5) or saline buffer (n=4). The primary injections were given in CFA supplemented with 200 µg m-BSA. These were followed by two-booster injections in IFA and m-BSA at day 15 and 45 after primary injection. The mice were weighed and bled one week after each immunisation. On day 45, males injected with RI-GnRH conjugate or saline were placed with females of proven fertility and litters observed. The males were sacrificed 75 days after primary injection for histological examination.

Second Mice Example (Example 2)
In the second experiment, four week old BALB/c mice (3 of each sex) were immunised with 25 µg/mouse unconjugated RI-GnRH coinjected with CpG (50 µg/mouse) oligonucleotide and m-BSA. A control group (2 of each sex) received saline buffer together with 50 µg/mouse CpG oligonucleotide as adjuvant (Klinman, et al., 1999) supplemented with 200 µg m-BSA. All injections were given in 10% v/v IFA. Mice were immunised at days 1, 15 and 30. They were bled and mated with partners of proven fertility at day 37 after the initial immunisation.

Antibody Purification

Serum from rabbits immunised with RI-GnRH was precipitated with saturated ammonium sulphate solution (40%) and dialysed overnight at 40° C. against PBS (pH=7.4). Sepharose 4B beads (1 mg) with activated thiol groups was used to couple 4 mM of RI-GnRH according to the standard procedures. Immunoglobulins were diluted 15 times to a final concentration of 10 mg/ml and passed through the column (100 µl/min) for three hours at 40° C. The anti-RI-GnRH antibodies were successively eluted with potassium thiocyanate (3M KSCN), glycine (2 M, pH=2.8), acetic acid (1% CH$_3$COOH and 3M NaCl, pH=2.1) and guanidium hydrochloride (6 M G-HCl). Two successive fractions of anti-RI-GnRH antibodies were eluted with potassium thiocyanate (KSCN 1 and 2) and one fraction was eluted for each of the other chaotropic agents. All fractions were immediately dialysed over night at 40° C. against PBS and checked with spectrophotometric analyses.

Enzyme Linked Immunoassay (ELISA)

Microtitre plates were coated with RI-GnRH peptide (5 µg/ml) in 100 mM Na$_2$CO$_3$ (pH=9.6) and incubated for one hour at 37° C. After several washes with PBS (pH=7.4) plates were saturated for one hour with 1% BSA in PBS supplemented with Tween 20 (0.1% wt/volume) at 37° C. Sera from immunised rabbits and mice at different dilutions (1:500 to 1:3200) were added to the plates and incubated for one hour at 37° C. Plates were washed several times and allowed to react with peroxidase-conjugated goat anti-rabbit or goat anti-mouse antibody (affinity purified Fc specific IgG) for one hour at 37° C. Washed plates were reacted with 3,3',5,5'-tetramethyl benzidine (TMB) and hydrogen peroxidase as substrate.

Inhibition Immunoassay

An inhibition immunoassay was used to test whether native GnRH, [Gln$^8$]GnRH, or GnRH II could displace purified rabbit anti-RI-GnRH antibodies from binding to fixed RI-GnRH. Nonspecific inhibition was determined with an unrelated L peptide, Val-Arg-Thr-Val-Glu-Asp-Gly-Glu-Cys (V9C), and an unrelated RI peptide (Asp-Ser-Leu-Arg-Asn-Leu-Met-Glu-Cys). Various dilutions of anti-RI-GnRH antibodies were preincubated with increasing concentrations of peptide (3.9-1000 nM) for 1 h at 37° C. The percent inhibition of signal was calculated from the amount of anti-RI-GnRH antibodies that bound RI-GnRH in the presence of increasing peptide concentrations against the amount of anti-RI-GnRH antibodies that bound RI-GnRH in the absence of competing peptide. This immunoassay was also used to test whether native GnRH could displace anti-RI-GnRH antibodies in mouse sera binding to fixed RI-GnRH. Various dilutions of serum samples were preincubated with increasing concentrations (3.65 pM to 20 nM) mammalian GnRH (GnRH) for one hour at 37° C.

Surface Plasmon Resonance (SPR)

The characterization of binding kinetics of rabbit anti-RI-GnRH antibody binding to RI-GnRH and GnRH was performed with SPR. The RI-GnRH peptide was fixed on a sensor chip (BIACORE, Uppsala, Sweden) by the standard thiol immobilisation protocol using the upgraded BIA 1000 (Pharmacia Biotech). Affinity purified rabbit anti-RI-GnRH antibodies were injected at a flow rate of 5 μl/min and a total volume of 100 μl over the sensor chip. Anti-RI-GnRH antibodies (50 nM) preincubated with either RI-GnRH (0.01-500 nM) or GnRH (15-5000 nM) for 15 min at room temperature were also injected under the same conditions described above. The sensorgrams were recorded and analysed by BiaEvaluation 3 software (BIACORE).

Transfection and Cell Culture

The human GnRH receptor gene was cloned into a mammalian expression vector, pcDNA I/AMP (Invitrogen, San Diego, Calif.) using EcoRI and XhoI, and transformed into competent XL-1 blue E. coli. Plasmid DNA was extracted from PC100 or PC500 kits (Machery-Nagel, Duren, Germany) from ampicillin-resistant clones and manually sequenced to check for the nucleotide sequence of the human GnRH receptor (Epicentre Technologies, Madison, Wis.).

COS-1 cells were cultured in Dulbecco's modified Eagle's medium/DMEM (Life Technologies, Inc., Paisley, Scotland), supplemented with 10% foetal calf serum (FCS, Delta bioproducts, Kempton Park, South Africa) in a 10% $CO_2$ incubator at 37° C. Cells were harvested with 0.05% trypsin. For all transient transfections $2 \times 10^5$ cells/well were seeded into 12-well plates and cultured overnight in DMEM containing 10% FCS and antibiotics (2 mg/ml streptomycin sulphate, 4000 U/ml sodium benzyl penicillin). COS-1 cells were transiently transfected using the DEAE-Dextran method [10], as previously described [15].

Phosphatidyl Inositol Hydrolysis

The transfected COS-1 cells ($2 \times 10^5$ cells/well) were incubated overnight in 0.5 ml Medium 199 (Life Technologies Inc.) with antibiotics and myo-[2-$^3$H] inositol (1 μCi/well, Amersham Pharmacia Biotech) as previously described [15]. The labelled cells were incubated with various concentrations of GnRH-analogs for one hour at 37° C. in the presence of LiCl as described [15]. Aspirating the medium and addition of 10 mM formic acid (1 ml/well) terminated the incubation. Inositol phosphates separated from the formic acid extract on DOWEX-1 ion exchange columns and eluted into scintillation liquid (Quicksafe, Zinsser Analytical, Frankfurt, Germany) and the radioactivity was counted.

Antiserum Inhibition of GnRH Stimulated Phosphatidyl Inositol Accumulation

Serum from rabbits immunised with RI-GnRH peptide was tested for its ability to inhibit GnRH stimulated IP accumulation in COS-1 cells transiently transfected with human GnRH receptor. Serum from the same rabbits before immunisation was also tested. Serum was diluted 1:250 in buffer containing various concentrations of GnRH (1 and 10 nM). This mixture was incubated for two hours at 37° C. before adding to the cells transfected with human GnRH receptor. After one hour the incubation was terminated with formic acid and inositol phosphates were separated and counted as described.

The ability of the purified anti-RI-GnRH antibody eluted fractions to inhibit GnRH-, [Gln$^8$]GnRH-, and GnRH II-stimulated IP production was determined as described above. The effective antibody concentration was calculated by incubating increasing concentrations of purified anti-RI-GnRH antibody fractions (0.1-5 nM) with 0.3 nM GnRH for 2 hours at 37° C. in buffer. The mixture was added to labelled cells, and the inhibition of IP production was calculated. The amount of purified anti-RI-GnRH antibody needed to inhibit at least 50% of the 0.3 nM GnRH stimulated IP accumulation was 5 nM. Purified anti-RI-GnRH antibodies were tested for their ability to discriminate among GnRH, [Gln$^8$]GnRH, and GnRH II. The purified antibody fractions (5 nM) were incubated with 0.3 nM GnRH, 1 nM [Gln$^8$]GnRH, and 1 nM GnRH II. Stimulating with these concentrations [half-maximal effective concentrations (EC50)] in the absence of antibody produced similar levels of IP counts. Additionally, purified anti-RI-GnRH antibody (0.1-5 nM) was preincubated with increasing concentrations of GnRH (0.1-1000 nM) for two hours at 37° C. in buffer. The mixture was added to labelled cells and the inhibition of IP production calculated as described.

Histology

Male mice were sacrificed and the testes dissected. Testes were weighed and fixed in formalin/saline solution (12%) for routine histology. The fixed testes were dehydrated, sectioned (5 μm thick) and stained with haematoxylin and eosin.

Data Reduction

IP assays were performed in duplicate and four-parameter nonlinear curve fitting (PRISM, GraphPad Software, In., San Diego, Calif.) was used to estimate the peptide concentrations required to stimulate half-maximal IP production ($EC_{50}$). The formulae for the sigmoidal dose-response curves (unweighted) was defined as Y=bottom+(top−bottom)/(1+10^(X−log $EC_{50}$)) (PRISM, version 3.0, GraphPad Software, Inc.). All kinetic analysis was performed with BiaEvaluation 3 (BIACORE) software, using the standard $\chi^2$ statistic test. The mouse anti-RI-GnRH antibody affinities for GnRH were defined as $1/IC_{50} \times$ antibody dilution ($IC_{50}$ is the 50% inhibitory concentration). All statistical analyses were performed with StatView, using a standard correlation program.

Immunised Rabbits Develop Antibodies Against RI-GnRH and GnRH

Both immunised rabbits produced high titre anti-RI-GnRH polyclonal antibodies. As shown in FIG. 1, different populations of antibodies with different affinity for RI-GnRH peptide and native GnRH were detected and purified. Antibody populations eluted by chaotropic agents such as acid glycine, $CH_3COOH$—NaCl and G-HCl recognised the RI-GnRH peptide with higher affinity than those eluted with KSCN. This shows the heterogenous nature of the raised polyclonal antibodies.

Figure 2A:
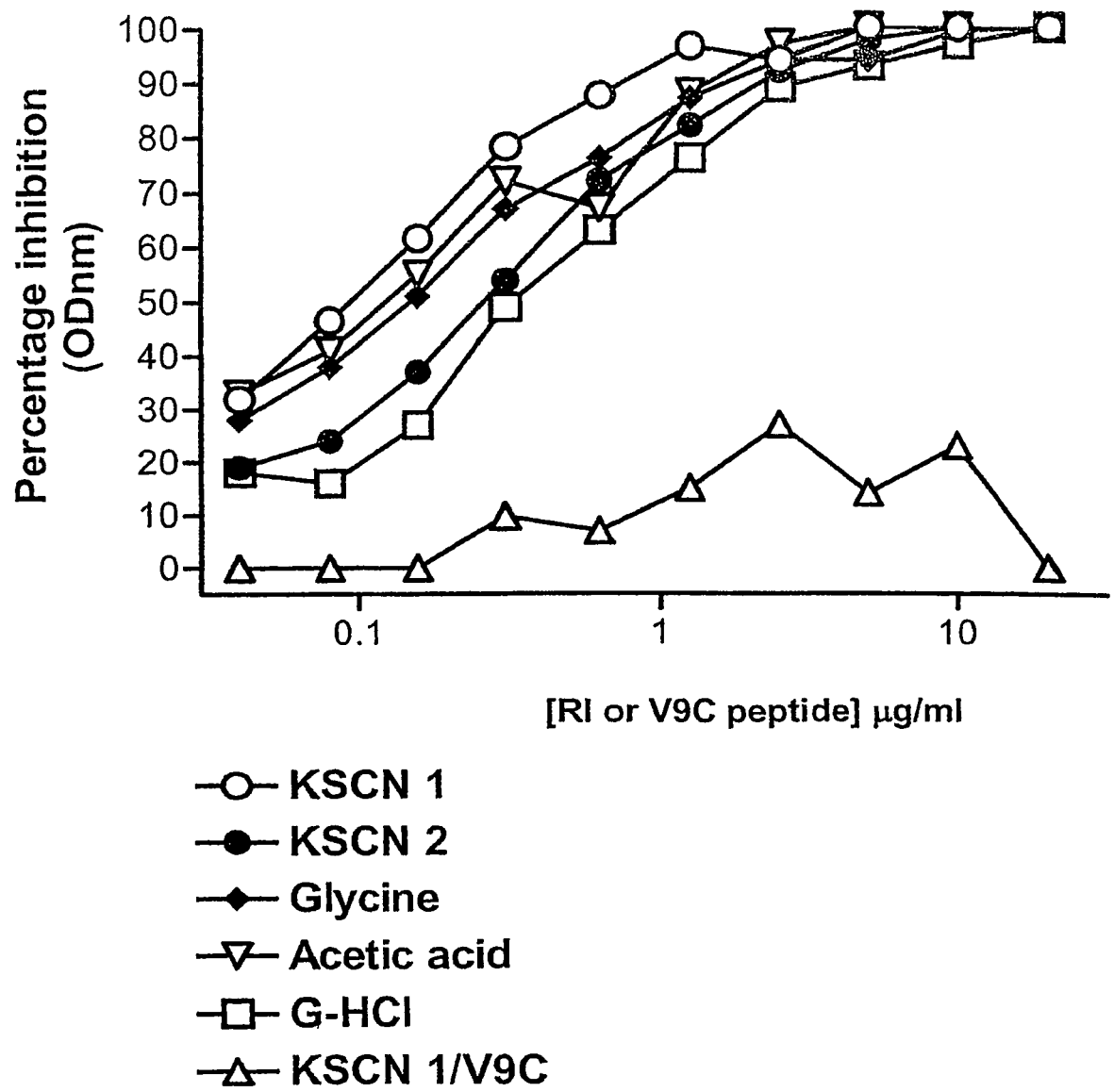
FIG. 2a Purified rabbit anti-RI-GnRH antibodies react with RI-GnRH peptide with high specificity. RI-GnRH was immobilized on ELISA plates and incubated with purified anti-RI-GnRH antibodies. Adding free RI-GnRH peptide to this reaction suppressed the amount of anti-RI-GnRH antibodies that could bind immobilized RI-GnRH. Antibodies eluted by various chaotropic agents are indicated by symbols. KSCN1 (○), KSCN2 (•), glycine (♦), acetic acid-NaCl (∇) and G-HCl (□). A non-related peptide (V9C, Δ) showed low inhibition of binding of the KSCN antibody fraction to RI-GnRH.

Anti-RI-GnRH antibodies in all eluted fractions bound the fixed RI-GNRH peptide on ELISA plates. Increasing amounts of free RI-GnRH peptide incrementally decreased the amount of anti-RI-GnRH antibodies available to bind the fixed RI-GnRH peptide on ELISA plates (FIG. 2a). The anti-RI-GnRH antibody binding was not significantly inhibited by unrelated L-peptide sequence, VRTVEDGEC (SEQ ID NO:6) (V9C). This suggests that these antibodies bind the RI-GnRH-peptide sequence with high specificity (FIG. 2a).

Figure 2B:
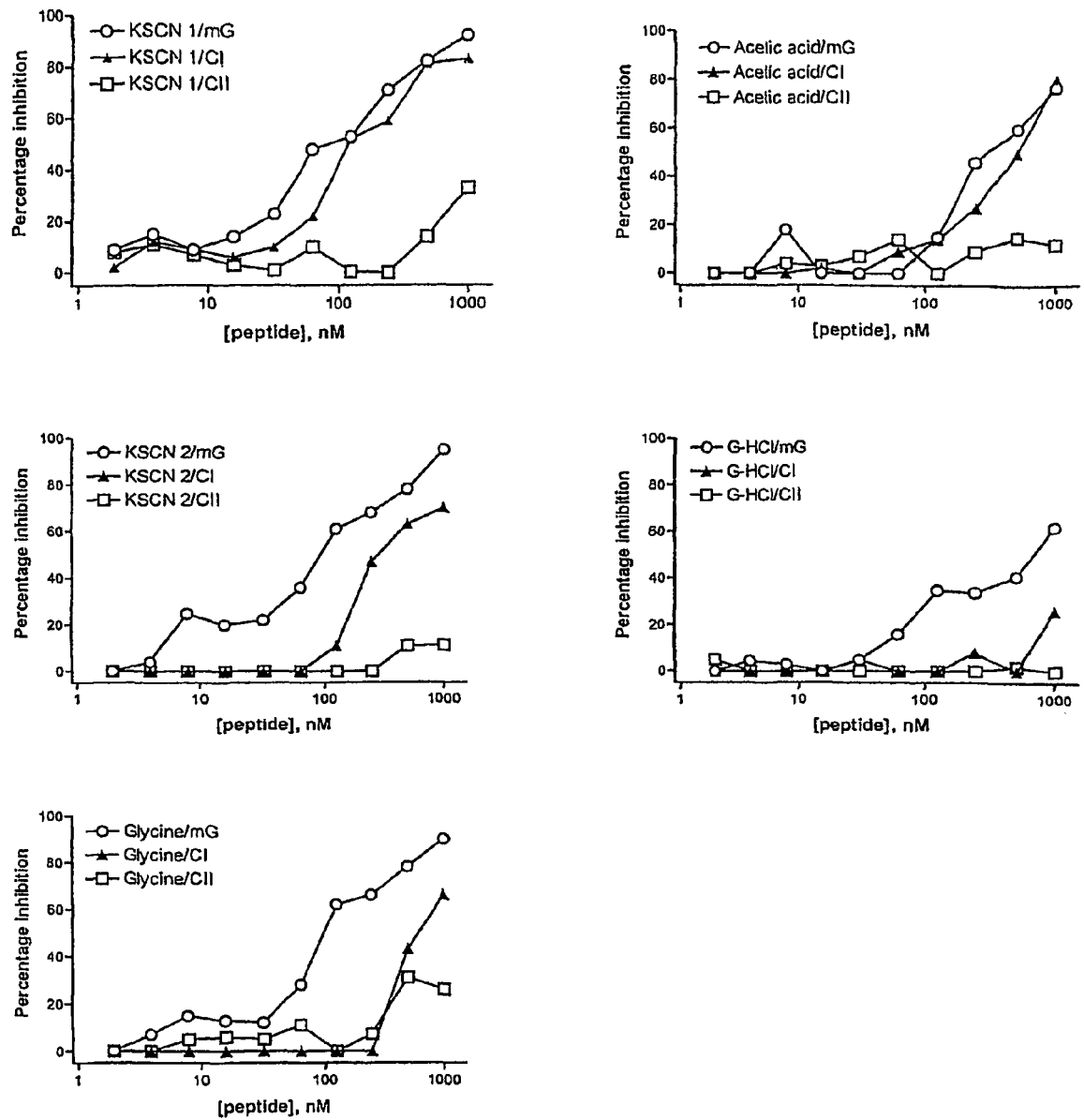
FIG. 2b Purified rabbit anti-RI-GnRH antibody fractions discriminate GnRH from related analogs. RI-GnRH peptide was immobilised on ELISA plates. The graph shows that for the various elutions (with KSCN and glycine, acetic acid-NaCl and G-HCl) the amount of purified anti-RI-GnRH antibodies which could bind to the fixed RI-peptide was suppressed by adding increasing concentrations of free GnRH (○), [Gln$^8$]-GnRH (▲) and GnRH II (□).

Native GnRH could also inhibit the different eluted fractions of anti-RI-GnRH antibodies from binding to the immobilised RI-peptide (FIG. 2b). This demonstrates that the anti-RI-GnRH antibodies cross-react with the parent L-amino acid sequence. Of the entire set of eluted antibody fractions, the KSCN fractions cross-reacted most efficiently with GnRH (FIG. 2b). This suggests that the KSCN eluted fraction of antibodies have the highest affinity for GnRH. The antibodies cross-reacted with GnRH with higher affinity compared with two GnRH related analogs ([Gln$^8$]-GnRH and GnRH II). These analogs have one ([Gln$^8$]-GnRH) and three ([His$^5$Trp$^7$Tyr$^8$]-GnRH) amino acid substitutions, respectively. This demonstrates that anti-RI-GnRH antibodies discriminate GnRH from related isoforms (FIG. 2b).

Binding Kinetics of Two anti-RI-GnRH Antibody Fractions

Figure 3A:
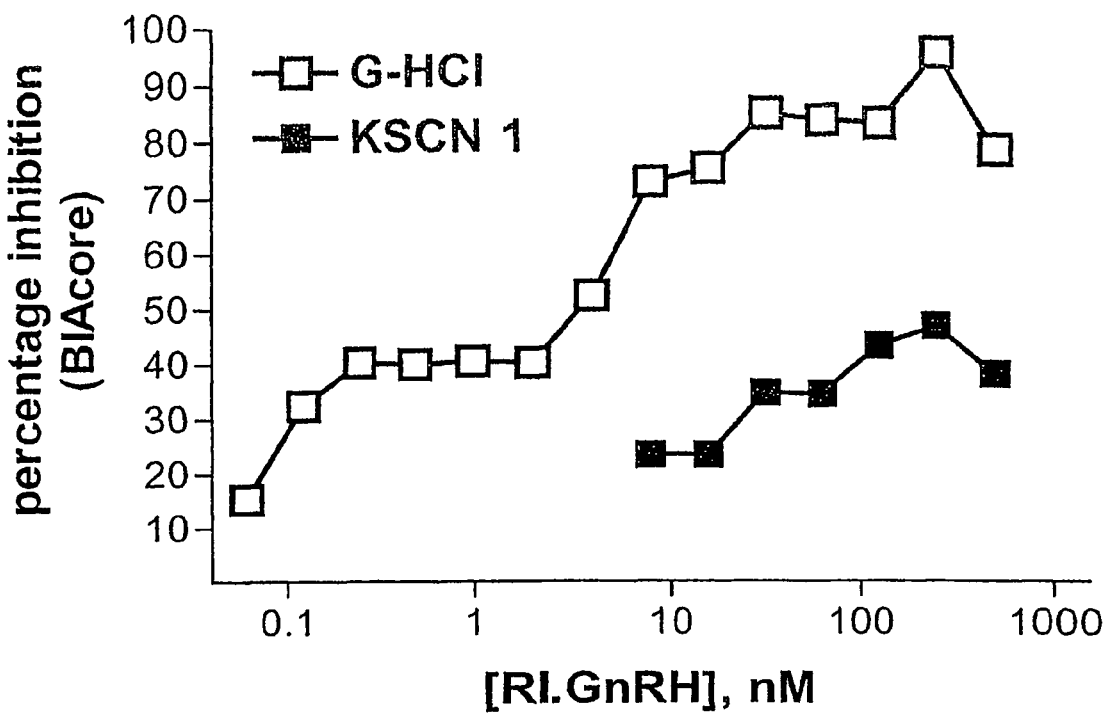
FIG. 3 The ability of purified anti-RI-GnRH antibodies to interact with GnRH and RI-GnRH was measured with BIO-CORE. RI-GnRH peptide was immobilised to the sensor chip. The amount of anti-RI-GnRH antibody binding to RI-GnRH peptide was measured in resonance units (RU) and was suppressed by adding increasing concentrations of RI-GnRH-peptide (a) or GnRH (b). Two eluted antibody fractions were tested, KSCN (■) and G-HCl (□).
Figure 3B:
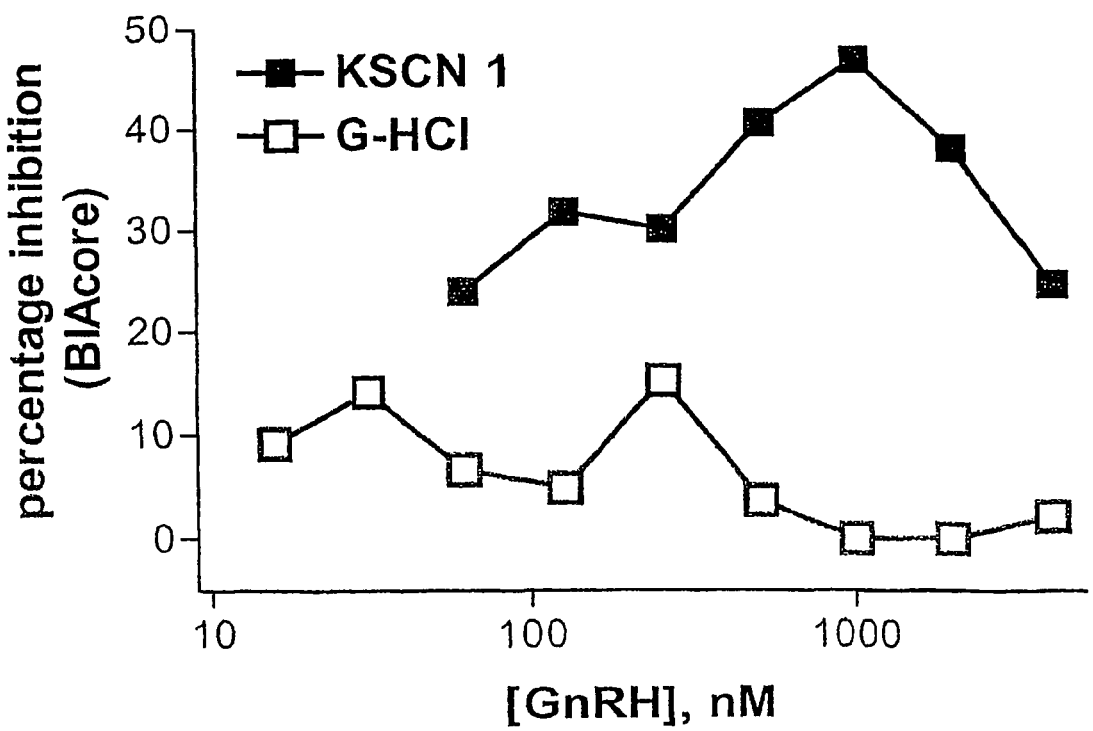

The binding kinetics of the G-HCl— and KSCN 1-purified antibody fractions were measured with the BIACORE instrument. The antibody fraction eluted with G-HCL had more than 40-fold higher affinity for RI-GnRH ($K_a=5.38\times10^8$ M$^{-1}$; $K_d=1.86\times10^{-9}$ M) than the KSCN 1 fraction ($K_a=2.89\times10^3$ M$^{-1}$; $K_d=9\times10^{-8}$ M). The amount of anti-RI-GnRH antibody binding to RI-GnRH peptide immobilised on the sensor chip was inhibited more by free RI-GnRH preincubated with the G-HCL antibody fraction than with the KSCN1 antibody fraction (FIG. 3a). This suggests that the G-HCl eluted antibody fraction is more specific for RI-GnRH peptides. Conversely, GnRH could suppress the KSCN1 antibody fraction from binding the RI-GnRH peptide (immobilised on the sensor chip) more effectively than the G-HCl antibody fraction (FIG. 3b). This indicates that the KSCN1 fraction has the highest antigenic cross-reactivity with native GnRH. The fact that the presentation of the amino acid side-chains in a RI analog can be very similar to that in the parent peptide suggests that the KSCN antibody fractions recognize the native GnRH peptide side-chains with the highest specificity.

Figure 4A:
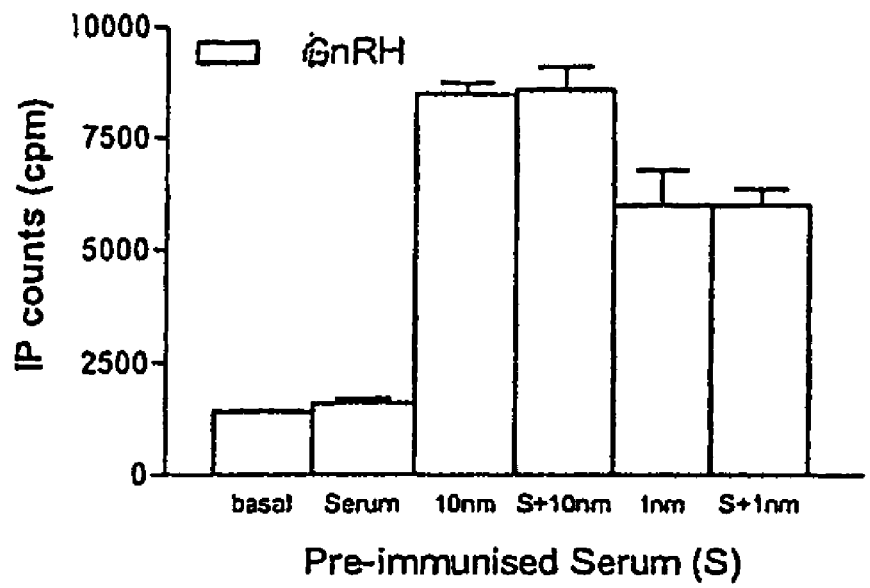
FIG. 4a Immunised rabbit serum inhibits GnRH stimulated IP accumulation. Effect of preimmune serum (S) from rabbits before immunisation on GnRH (1 nM and 10 nM) accumulation in COS-1 cells transiently transfected with human GnRH receptor (top panel). Inhibition of GnRH (1 nM and 10 nM) stimulated IP accumulation with serum collected from rabbits immunised with RI-GnRH (bottom panel).
Figure 4A:
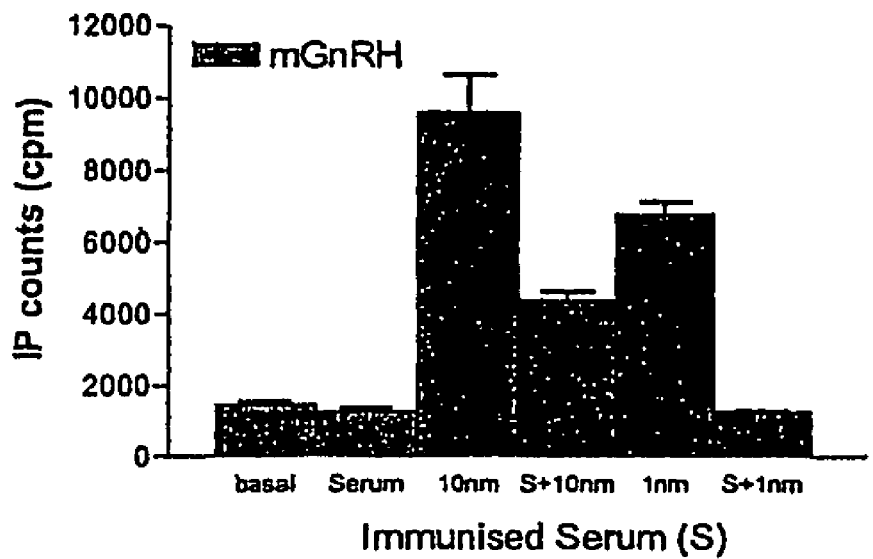

Anti-RI-GnRH Antibodies Inhibit GnRH Stimulated Inositol Phosphate Accumulation Serum collected from the rabbits immunised with RI-GnRH peptide could inhibit GnRH stimulated inositol phosphate (IP) accumulation in COS-1 cells transiently transfected with human GnRH receptor (FIG. 4a). Serum from the same rabbits before immunisation had no effect on GnRH stimulated IP accumulation.

Figure 4B:
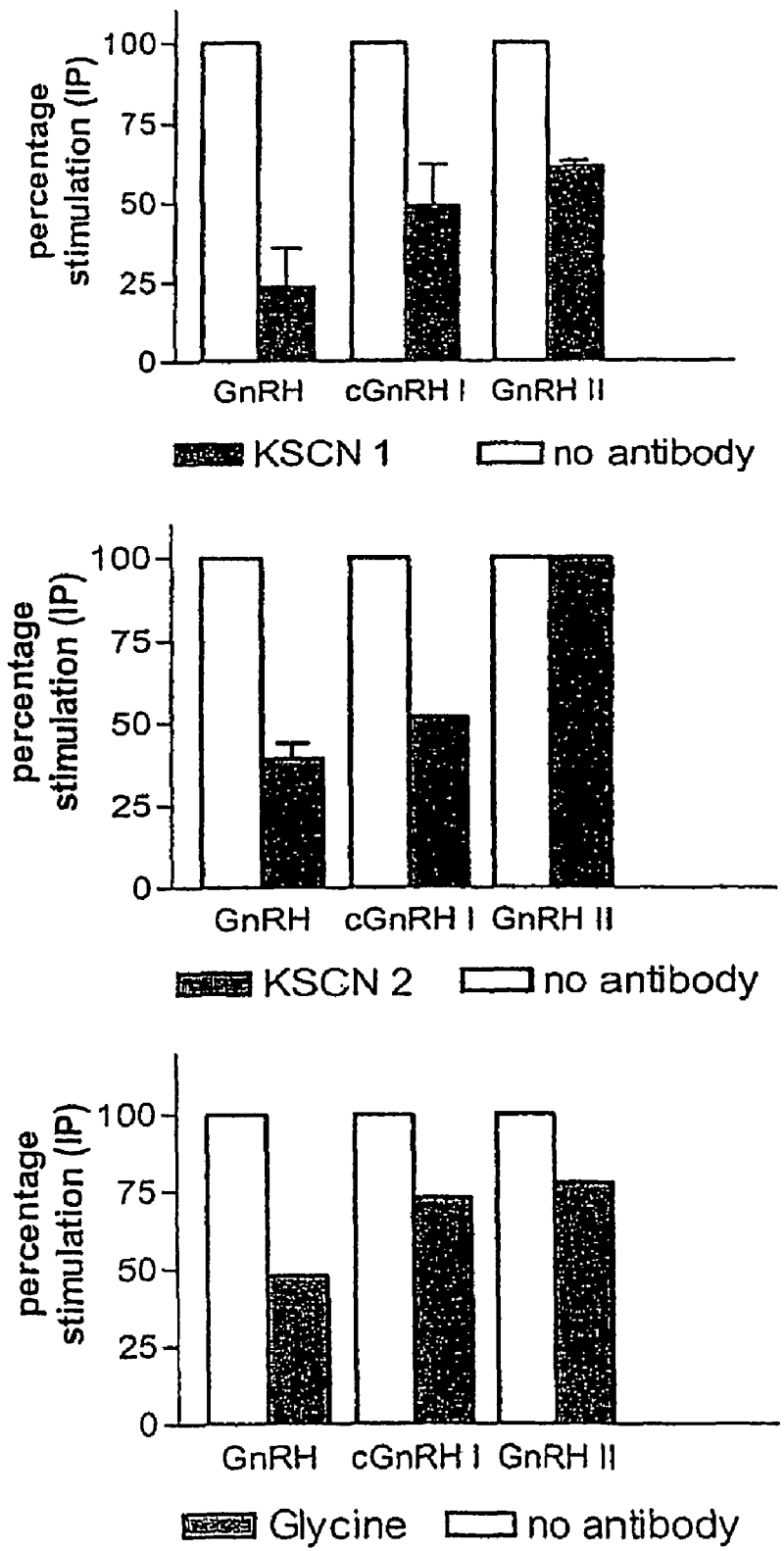
FIG. 4b Purified rabbit anti-RI-GnRH antibodies selectively inhibit GnRH stimulated IP accumulation. COS-1 cells transfected with the human GnRH receptor were incubated separately with 0.3 nM GnRH, 1 nM [Gln$^8$]GnRH, and 1 nM GnRH II, which were preincubated with 5 nM anti-RI-GnRH antibody fractions KSCN 1, KSCN 2, and glycine (solid shading). The effect of the antibodies on ligand stimulated IP accumulation was calculated as a percentage inhibition of ligand stimulated IP accumulation in the absence of antibody (open columns).

The ability of the different anti-RI-GnRH antibody eluted fractions to inhibit GnRH, [Gln$^8$]-GnRH and GnRH II stimulated IP accumulation was compared (FIG. 4b). The KSCN eluted antibody fractions were the most effective in inhibiting GnRH stimulated IP accumulation than was the glycine eluted antibody fraction. The $CH_3COOH$—NaCl and G-HCl eluted antibody fractions did not inhibit GnRH stimulated IP production. This suggests that KSCN eluted antibody fractions have the highest level of antigenic cross-reactivity with the parent L-peptide as observed in the binding studies. Additionally, the RI-GnRH peptide alone could not stimulate or inhibit GnRH stimulated IP accumulation (data not shown). This shows that the RI-GnRH peptide would have no additional effect on GnRH function, other than acting as an immunogen raising neutralising GnRH antibodies.

The highest available antibody concentration was 5 nM. Consequently, the antibody concentration inhibiting 50% of 0.3 nM GnRH-stimulated IP accumulation was calculated from sigmoidal dose-response curves. The $EC_{50}$ for the KSCN fraction was 1.7 nM, that for the KSCN 2 fraction was 1.4 nM, and that for the $CH_3COOH$—NaCl was 2.2 nM.

Figure 4C:
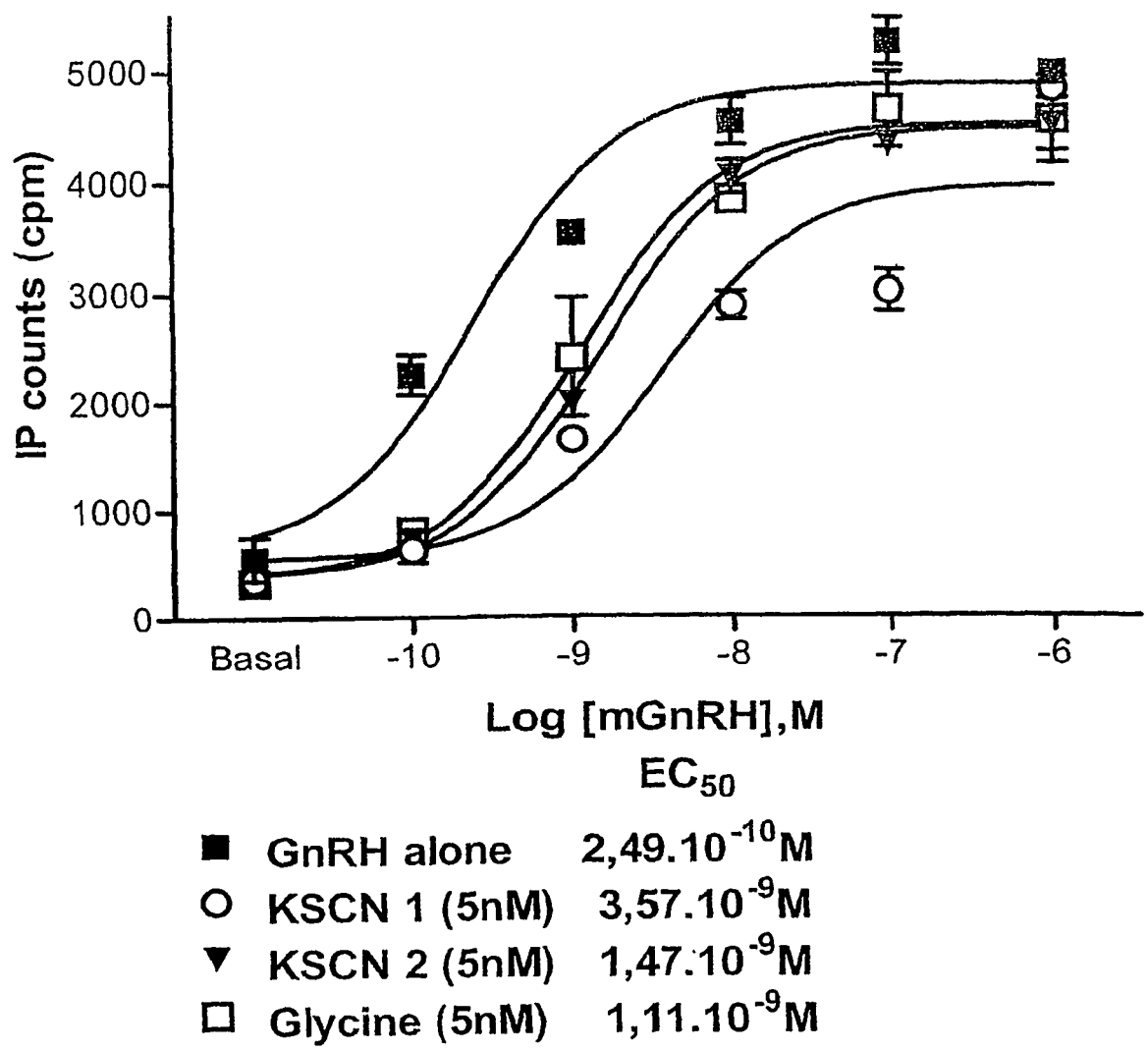
FIG. 4c Purified rabbit anti-RI-GnRH antibodies suppress increasing concentrations of GnRH-stimulated IP accumulation. Dose-response curves of GnRH-stimulated IP accumulation were measured in COS-1 cells transiently transfected with the human GnRH receptor. The $EC_{50}$ of GnRH (0.25 nM) was suppressed when 5 nM anti-RI-GnRH antibodies of KSCN (3.6 and 1.5 nM) and glycine (1.1 nM) fractions were pre-incubated with varying concentrations of GnRH.
Figure 4D:
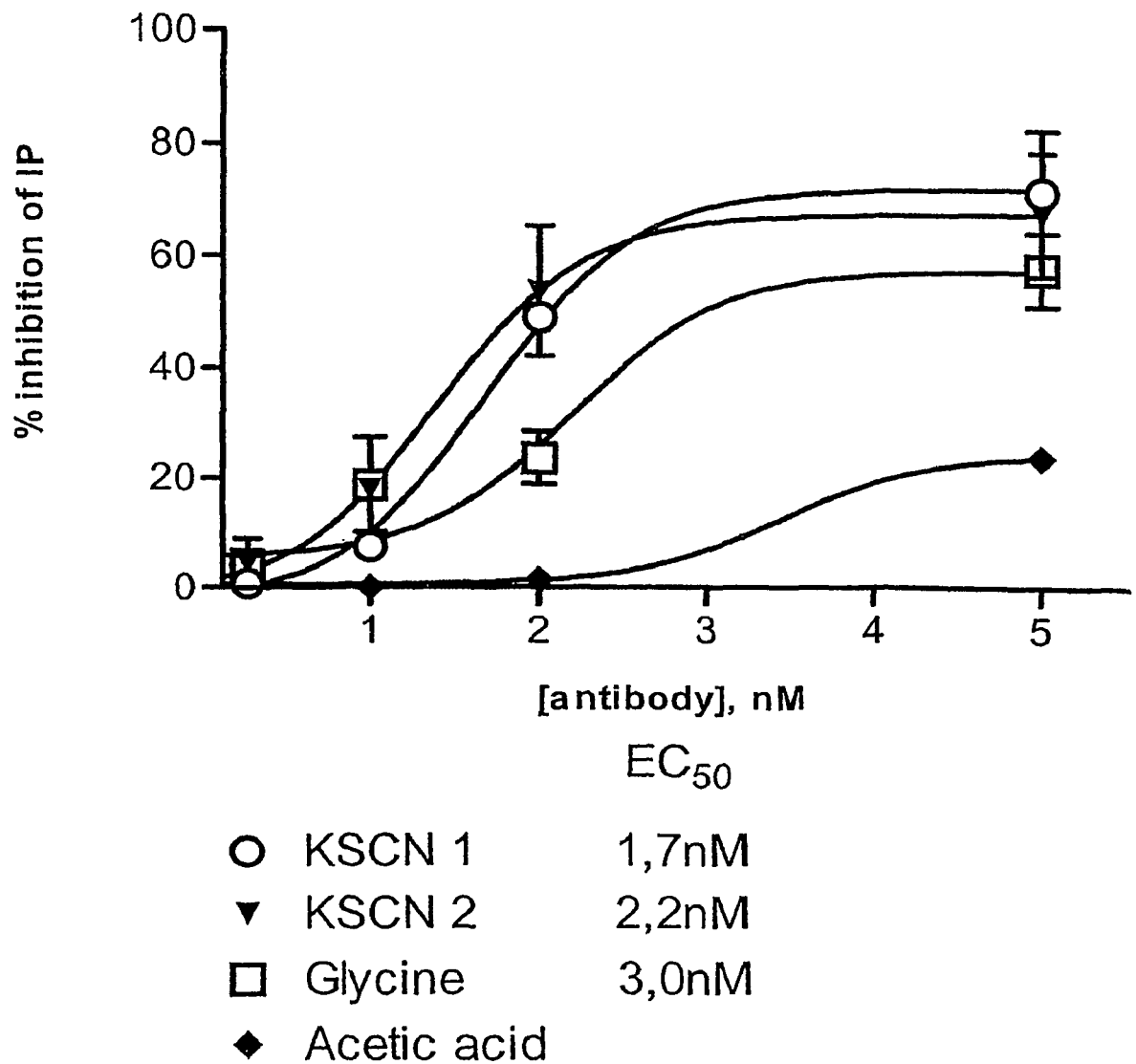
FIG. 4d Effect of increasing concentrations of purified rabbit anti-RI-GnRH antibody fractions on GnRH-stimulated IP accumulation. A fixed concentration of GnRH (0.3 nM) was preincubated with varying concentrations of rabbit anti-RI-GnRH antibody from different eluted fractions. The concentration of anti-RI-GnRH needed to inhibit 50% of the GnRH-stimulated IP accumulation in COS-1 cells transiently transfected with the human GnRH receptor was determined for fractions KSCN 1 (1.7 nM), KSCN 2 (1.4 nM), glycine (2.2 nm), and CH$_3$COOH—NaCl.

Incubating a fixed concentration (5 nM) of purified anti-RI-GnRH antibodies with varying GnRH concentrations suppressed GnRH-stimulated IP accumulation in COS-1 cells transiently transfected with the human GnRH receptor (FIG. 4c). The $EC_{50}$ values calculated (Prism, GraphPad Software Inc., San Diego) from dose-response curves of GnRH stimulated IP accumulation were compared with those for GnRH incubated with anti-RI-GnRH antibodies (FIG. 4c). Complete inhibition of GnRH-stimulated IP accumulation was not possible, as only a maximum concentration of 5 nM antibody was available. The $EC_{50}$ values of GnRH-stimulated IP accumulation were effectively suppressed by the KSCN 1-eluted (14.4-fold), KSCN 2-eluted (6.0-fold) and glycine-eluted (4.4-fold) antibody fractions (FIG. 4c). Increasing concentrations of purified antibody fractions from KCSN 1 and 2, glycine and $CH_3COOH$—NaCl elutions, progressively inhibited 0.3 nM GnRH stimulated IP accumulation in COS-1 cells transiently transfected with the human GnRH receptor (FIG. 4d). Most antibody fractions eluted with KSCN 1 elution were not effective and inhibited 0.1 nM GnRH-stimulated IP accumulation by more than 90% (FIG. 4d). The concentration of GnRH in the hypothalamic-hypophyseal portal system is similar to this.

RI-GnRH Immunised Mice Produce Antibodies which Inhibit Reproduction

Figure 5A:
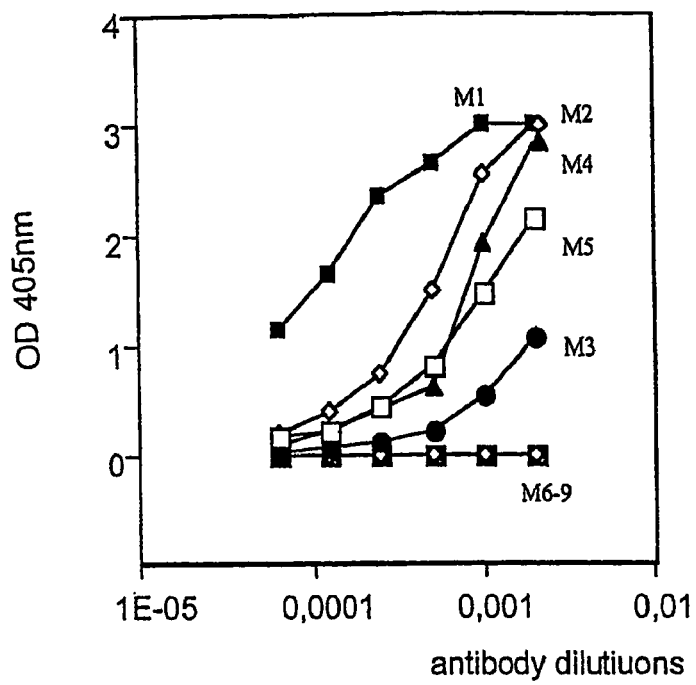
FIG. 5a Titre of anti-RI-GnRH antibodies raised in five male mice (M1-M5) immunised with RI-GnRH conjugated to MAO in CFA. Control mice (M6-M9) received only methylated BSA in CFA. Methylated BSA in CFA was used with RI-GnRH in the booster injections for test animals.
Figure 5B:
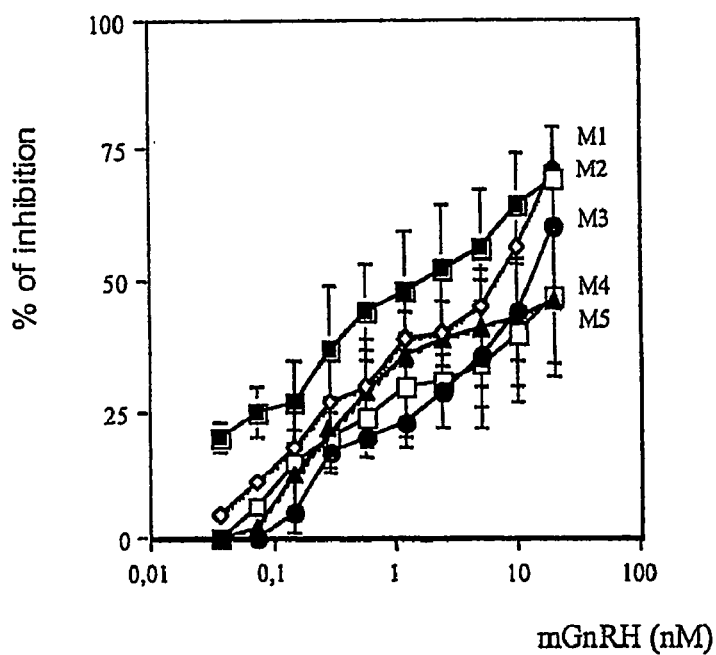
FIG. 5b Inhibition of binding of mouse anti-RI-GnRH sera to RI-GnRH by increasing concentrations of m-GnRH in experiment 1. RI-GnRH was immobilised on ELISA plates and incubated with serum collected on day 22 after initial mating in the presence of increasing concentrations of native GnRH.
Figure 6A:
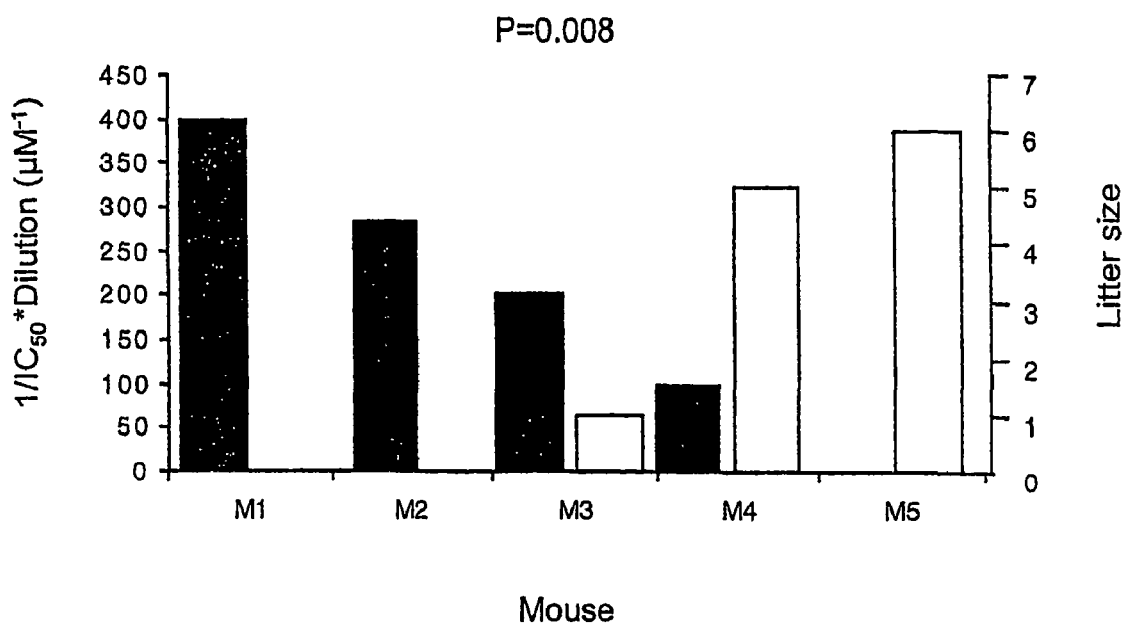
FIG. 6a Immunising male mice with RI-GnRH peptide decreases their fertility in the first mouse experiment. Relationship between anti-RI-GnRH affinity for GnRH and litter size of normal females mated with immunised male mice.
Figure 6B:
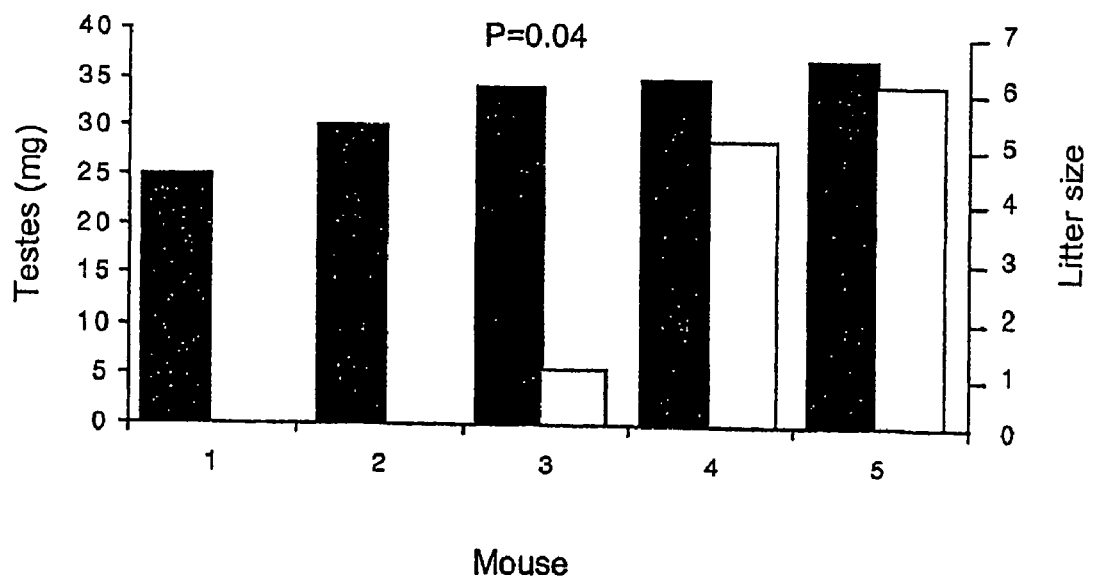
FIG. 6b Relationship between testis weight of immunised male mice and litter size of normal females mated with them in the first mice experiment.

All five immunised male mice developed anti-RI-GnRH antibodies (FIG. 5a) and the five of highest titre also bound native GnRH (FIG. 5b). Two of the group of five immunised mice were infertile, one mouse fostered one pup and the remaining two had four and five pups respectively. There was a correlation between antibody titre and $IC_{50}$ with the suppression of fertility. The highest affinity for GnRH was detected in the infertile mice while the lowest was in the fertile ones (P=0.008, FIG. 6a). Testis weight was directly related to litter size (P=0.004, FIG. 6b). Mating of control male mice with normal females results in normal litter size (5-7 pups). Testis weight was also directly related to litter size.

Figure 7:
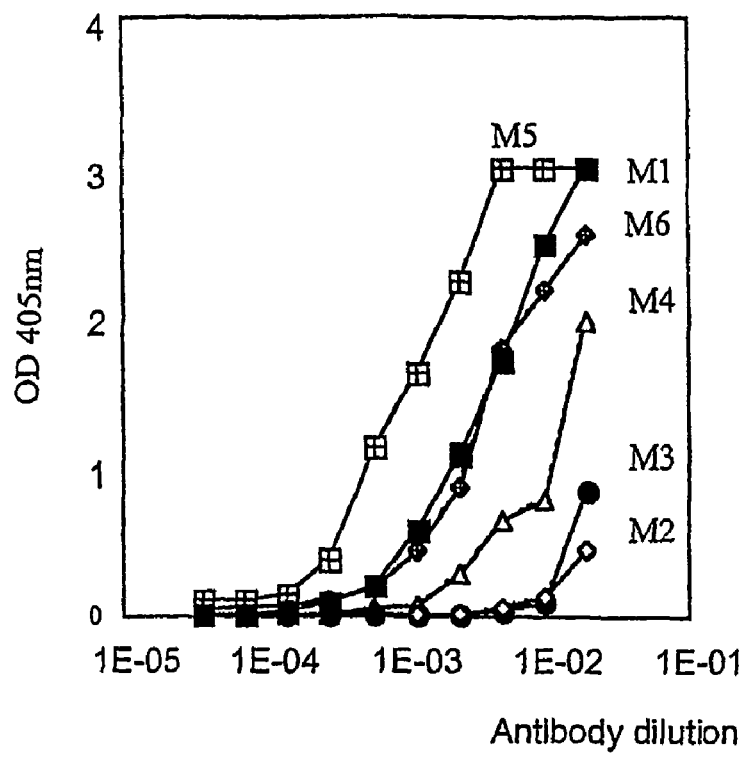
FIG. 7 Titre of anti-RI-GnRH sera from mice from the second mice experiment which are immunised with RI-GnRH and CpG but without FCA. M1, M3 and M4 are males, M2, M5 and M6 were females.
Figure 8:
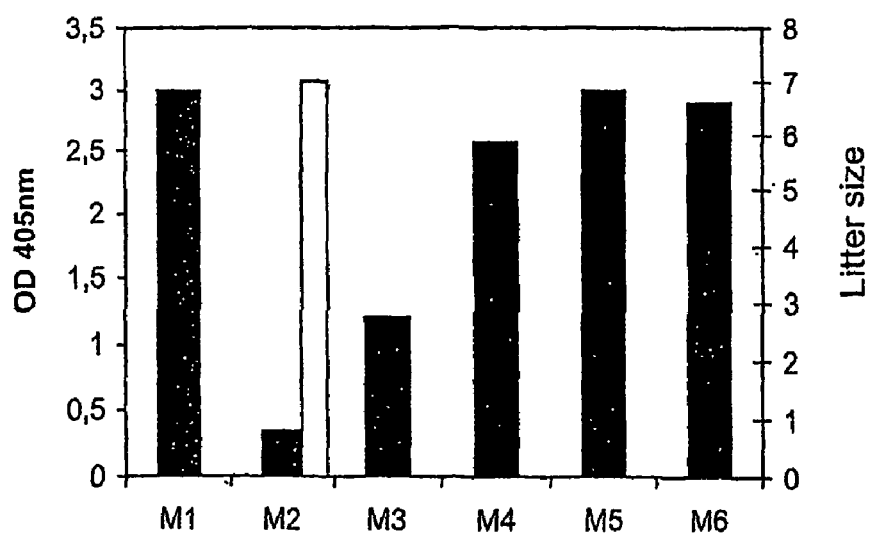
FIG. 8 Second mice experiment: Relationship between anti-RI-GnRH titre and litter size resulting from pairing of RI-GnRH CpG immunised male (M1, M3, M4) and female (M2, M5, M6) mice with normal partners. Solid columns are titre, open columns are litter size.

In the second example, mice immunised with RI-GnRH peptide and CpG as adjuvant produced anti-RI-GnRH antibodies, which cross-reacted with the native hormone (FIG. 7). All mice were infertile after pairing at day 37, except for one, which had a delayed immune response to RI-GnRH (FIG. 8). Infertility persisted after the initial mating as there were no litters resulting from further matings up to day 90. The mice were boosted once more at day 97 and mated one week thereafter (Table 1). Two mice were infertile on day 120, while four mice stayed infertile until day 220, when they were sacrificed. Infertility was related to the titre of anti-RI-GnRH (Table 1). Control female mice had normal litter size and female partners of control male mice also had normal litter size. In both examples there was no indication of adverse side effects or changes in body weight of the mice.

TABLE 1

RI-immunized mice produce RI-GnRH antibodies without complete Freund's adjuvant

| Mouse | Sex | Titre 1 (d 37) |
|---|---|---|
| 1 | Male | 3.00E−05 |
| 2 | Male | 1.00E−03 |
| 3 | Female | 1.00E−02 |
| 4 | Male | 5.00E−04 |
| 5 | Female | 3.00E−05 |
| 6 | Female | 1.30E−04 |

Histological evaluations of sections of the testes of mice treated with RI-GnRH peptide revealed atrophied Leydig and Sertoli cells, less spermatogonia and primary spermatocytes, presence of very few spermatids and reduced diameters of the seminiferous tubules. These results indicate suppressed spermatogenesis in the immunised infertile mice.

Thus, an RI peptide has been shown to be an effective synthetic GnRH vaccine.

Immunisation of experimental animals with a RI-GnRH peptide elicited polyclonal anti-RI-GnRH antibody production in rabbits and mice, which possess a high level of antigenic cross-reactivity with the parent L-amino acid peptide, GnRH. The level of anti-RI-GnRH antibodies produced in sera was detected with ELISA and both RI-GnRH and native GnRH bound the antibodies. Sera containing anti-RI-GnRH antibodies were able to effectively inhibit GnRH stimulated IP accumulation in COS-1 cells transiently transfected with the human GnRH receptor. The RI-GnRH peptide did not stimulate or inhibit GnRH stimulated IP accumulation. This suggests that the RI-GnRH peptide would not affect GnRH receptor function, except by eliciting production of antibodies which immunoneutralise endogenous GnRH.

Clearly the antisera were not against the N and C termini of RI-GnRH, as these would not recognize native GnRH. As the antibodies cross-react less with [Gln8[GnRH and GnRH II, which differ in structure in the central region ($Gln^8$ and $His^5$, $Trp^7$, $Tyr^8$, respectively), it appears that the antibodies are directed at this region. Their ability to immunoneutralize GnRH suggests that binding the central region sterically impairs access of the N and C termini to the receptor.

Antibodies from whole serum were precipitated and the anti-RI-GnRH antibodies were affinity purified and characterised with ELISA and the upgraded BIACORE1000 system [25]. Immunising with RI-GnRH peptide thus produces anti-RI-GnRH and GnRH antibodies with varying affinities and specificities. The antibodies with the highest affinity for RI-GnRH peptide had, as expected, the lowest cross-reactivity with the native GnRH while the lower affinity antibodies cross-reacted well with native GnRH. Nevertheless, the lower affinity anti-bodies were more selective for mammalian GnRH than other naturally occurring forms ([$Gln^8$]GnRH and GnRH II) and are probably the main contributors to the suppression of fertility observed. The specificity of the antibodies against GnRH was encouraging as most vertebrate species have variant forms of GnRH which are thought to have physiological functions in addition to regulating pituitary hormone release [12;24]. For example, primates have both GnRH and GnRH II, of which GnRH II is predominantly found in extrahypothalamic areas [27;14] and is suggested to have a neuromodulator role [24;9]. The mammalian pituitary GnRH receptor is proposed to discriminate between GnRH related peptides [12]. To specifically inhibit the reproductive system, it is desirable that antibodies raised against RI-GnRH do not cross-react with GnRH II, as has been demonstrated.

The ability of the different purified anti-RI-GnRH antibody fractions to inhibit GnRH-, [$Gln^8$]GnRH-, and GnRH II-stimulated IP accumulation was compared in COS-1 cells transiently transfected with the human GnRH receptor (FIG. 4b). The KSCN 1-, KSCN 2-, and glycine-eluted antibody fractions inhibited GnRH-stimulated IP production more than that of GnRH II (compare with FIG. 2b). Moreover, the KSCN-eluted antibody fractions inhibited GnRH-stimulated IP accumulation better than the glycine-eluted antibody fractions. The $CH_3COOH$—NaCl-eluted antibody fractions did not inhibit any of the GnRH analog-stimulated IP production (data not shown). This suggests that KSCN-eluted antibody fraction cross-reacted the most with native GnRH and is consistent with the results of the inhibition ELISA (FIG. 2b) and BIACORE (FIG. 3b) experiments. Additionally, the RI-GnRH peptide alone could not stimulate or inhibit GnRH-stimulated IP accumulation in COS-1 cells transiently transfected with the human GnRH receptor (data not shown). This shows that the RI-GnRH peptide has no effect on GnRH receptor function, other than acting as an immunogen producing neutralizing GnRH-specific antibodies.

Some of the animals did not show a response to the RI-GnRH peptide, and further refinement to the vaccination procedure may be required, such as altering the frequency of immunisation or the dosage in order to obtain a better response in more animals.

The synthetic RI-GnRH peptide elicited high titres of anti-GnRH antibody and induced sterility in both male and female mice, with no noticeable side affects. Treatment lead to reduced testis weight and low fertilisation and pregnancy rates, which correlated directly with anti-RI-GnRH antibody titre, respectively. Histology of testes revealed atrophied Leydig and Sertoli cells, reduced diameters of the seminiferous tubules and the absence of elongated spermatids in their laminae, confirming the observed suppression of male fertility. These observations are consistent with an inhibition of gonadotropin secretion [13, 18].

It has been demonstrated that a peptide based GnRH vaccine is effective in inducing reversible infertility in humans, which is directly related to the antibody titre [22]. Another study demonstrated that a GnRH vaccine induced infertility in white-tailed deer lasting up to two years without boosting [17]. Since the RI-GnRH peptide was effective in mice it should have similar results to native GnRH vaccine in other mammals. Since D-amino acid peptides are resistant to proteases it should be active as an oral vaccine.

GnRH vaccines have been suggested to be most practical for use as companion animal contraceptives [13], animal husbandry [1], and controlling wild life populations [17]. Although GnRH vaccines also offer potential as contraceptive agents in humans, concerns over the reversibility and need to supplement sex hormones would have to be addressed. The most likely application in humans would be in the treatment of sex hormone dependent cancers [22].

The studies in male and female mice established that antibodies to RI-GnRH also bound the native GnRH peptide. Observations on pregnancy outcome of the matings of immunized male or female mice indicated an inhibition of fertility (data not shown). However, analysis of plasma pituitary and gonadal hormones was not undertaken.

These RI-GnRH immunogens have a number of potential advantages over previously published GnRH vaccination approaches that employ GnRH conjugated to carrier proteins and adjuvants that seriously compromise recipients. Firstly, immunization with RI-GnRH does not require conjugation to an immunogenic carrier protein, as the RI-GnRH is apparently not recognized as self, but is sufficiently similar to GnRH to produce GnRH-immunoneutralizing antibodies. Secondly, the RI peptides tend to produce higher titres. Thirdly when administered with the oligonucleotide CpG, antibodies are produced without the need for the traumatizing CFA. They are highly immunogenic and specific. Additionally, RI-peptides are protease resistant, suggesting that they may have oral activity, and if conjugated to bile salts, attenuated toxins (e.g. pertussis and cholera) and/or activity absorbed vitamins, may facilitate absorption across the gastro-intestinal tract, so eliciting a specific immunogenic response. Moreover, while the known GnRH peptide vaccines cannot be administered trans-cutaneously because the skin barrier limits the penetration of the high molecular weight GnRH peptides, the RI-peptides of the present invention have a sufficiently low molecular weight to be able to pass through the skin barrier and induce an immunogenic response. They are therefore also suitable for trans-cutaneous administration, such as in the form of a skin patch.

REFERENCES

1. Beekman N J, Schaaper W M, Turkstra J A and Meleon R H (1999), Highly immunogenic and fully synthetic peptide-carrier constructs targeting GnRH. *Vaccine* 17:2043-2050.

2a. Benkirane N, Guichard G, Briand J P, Muller S, Brown F and Van Regenmortel M H (1996), Mimicry of viral epitopes with retro-inverso peptides of increased stability. *Dev Biol Stand* 87:283-291.

2b. Benkirane N, et al. (1996). J. Bio. Chem. 271, 33218-33224.

3. Casper R F (1991) Clinical uses of gonadotropin-releasing hormone analogues. *Cmaj* 144:153-158.

4. Davidson J S, Wakefield I K, Sohnius U, van der Merwe P A and Millar R P (1990), A novel extracellular nucleotide receptor coupled to phosphoinositidase-C in pituitary cells. *Endocrinology* 126:80-87.

5. Ferro V, et al. Effects of adjuvant, dose and carrier pre-sensitisation on the immunisation efficacy of a GnRH analogue. Drug Des Discov. 1996 December; 14(3):179-92

6. Fink G (1988) Gonadotropin secretion and its control, in *The Physiology of Reproduction.x* (Knobil E and Neill J D, eds.) pp 1349-1377, Raven Press, New York.

7. Ghosh S and Jackson D C (1999) Antigenic and immunogenic properties of totally synthetic peptide-based antifertility vaccines. *Int. Immunol* 11:1103-1110.

8. Jacobs E, Watson S A, Michaeli D, Ellis I O and Robertson J F (1999) Anti-gonadotrophin releasing hormone antibodies inhibit the growth of MCF7 human breast cancer xenografts. *Br J Cancer* 80:352-359.

9. Jones S W (1987) Chicken II luteinizing hormone-releasing hormone inhibits the M-current of bullfrog sympathetic neurons. *Neurosci Lett* 80:180-184.

10. Keown W A, Campbell C R and Kucherlapati R S (1990) Methods for introducing DNA into mammalian cells. *Methods Enzymol* 185:527-537.

11. Klinman D M, et al. (19??). CpG motifs as immune adjuvants. Vaccine 17:19-25.

12. King J A and Millar R P (1995) Evolutionary aspects of gonadotropin-releasing hormone and its receptor. *Cell Mol Neurobiol* 15:5-23.

13. Ladd A, Tsong Y Y, Walfield A M and Thau R (1994) Development of an antifertility vaccine for pets based on active immunisation against luteinizing hormone-releasing hormone. *Biol Reprod* 51:1076-1083

14. Latimer V S, Rodrigues S M, Garyfallou V T, Kohama S G, White R B, Fernald R D and Urbanski H F (2000), Two molecular forms of gonadotropin-releasing hormone (GnRH-I and GnRH-II) are expressed by two separate populations of cells in the rhesus macaque hypothalamus. *Brain Res Mol Brain Res* 75:287-292.

15. Millar R P, Davidson J, Flanagan C A and Wakefield I (1995), Ligand binding and second messenger assays for cloned Gq/G11-coupled neuropeptide receptors; the GnRH receptor, in *Methods in Neurosciences, Receptor Molecular Biology* (Sealfon S C, ed.) pp 145-162, Academic press, San Diego.

16. Millar R P, King J A, Davidson J S and Milton R C (1987) Gonadotropin-releasing Hormone—diversity of functions and clinical applications. *S Afr Med J* 72:748-755.

17. Miller L A, Johns B E and Killian G J (2000) Immunocontraception of white-tailed deer with GnRH vaccine. *Am J Reprod Immunol* 44:266-274.

18. Moudgal N, et al. Development of male contraceptive vaccine-a perspective. Human Reproduction Update 1997, vol. 3, No. 4, pp 335-346.

19. Muller S, et al. (1995) Pept. Res. 8:138-144.

20. Muller S, et al. (1998) The potential of retro-inverso peptides as synthetic vaccines. Exp. Opin. Invest. Drugs 7(9): 1429-1438.

21. Talwar G P (1999) Vaccines and passive immunological approaches for the control of fertility and hormone-dependent cancers. *Immunol Rev* 171:173-192.

22. Talwar G P (1997) Vaccines for control of fertility and hormone dependent-cancers. *Immunol Cell Biol* 75:184-189.

23. Talwar G (1997). Fertility regulating and immunotherapeutic vaccines reaching human trials stage. Human Reproduction Update (1997), vol. 3, No. 4, pp 301-310.

24. Troskie B, King J A, Millar R P, Peng Y Y, Kim J, Figueras H and Illing N (1997) Chicken GnRH II-like peptides and a GnRH receptor selective for chicken GnRH II in amphibian sympathetic ganglia. *Neuroendocrinology* 65;396-402.

25. Van Regenmortel M, et al. Measurement of antigen-antibody interactions with biosensors. J. Mol. Recoqn. 11, 163-167, 1998.

26. Van Regenmortel M, (1997). In Vaccines 97, Cold Spring Harbor Laboratory Press, pp 9-15.

27. White R B, Eisen J A, Kasten T L and Fernald R D (1998) Second gene for gonadotropin-releasing hormone in humans. *Proc Natl Acad Sci USA* 95:305-309.

The invention claimed is:

1. A synthetic peptide comprising the amino acid sequence GPRLGYSWHX (SEQ. ID. No. 3), wherein each of the amino acids are in the D-amino acid configuration and X is any amino acid.

2. The peptide according to claim 1, wherein X is E, Q, P or G.

3. The peptide according to claim 1 comprising the amino acid sequence GPRLGYSWHE (SEQ ID NO:1).

4. The peptide according to claim 1, further comprising a D-amino acid cysteine residue at the C-terminus end.

5. The peptide according to claim 1, comprising the amino acid sequence GPRLGYSWHEC (SEQ ID NO:2).

6. The peptide according to claim 1 which is conjugated to another peptide.

7. The peptide according to claim 6, which is conjugated to the natural gonadotropin-releasing hormone (GnRH) peptide.

8. The peptide according to claim 1, wherein X is Q.

9. A peptide according to claim 1, which further comprises an additional D-amino acid residue at the N- or C-terminus.

10. The peptide according to claim 1, further comprising a D-amino acid cysteine residue or a glycine residue at the N- or C-terminus.

11. A vaccine composition capable of eliciting an immunological response in an animal to which it is administered, the composition comprising:

(a) an immunogenic peptide according to claim 1; and
(b) a pharmaceutically acceptable carrier or excipient.

12. The vaccine composition according to claim 11, wherein the peptide is not conjugated to or administered with a carrier or an adjuvant.

13. The vaccine composition according to claim 11, wherein the peptide is conjugated to or administered with at least one carrier or adjuvant.

14. The vaccine composition according to claim 13, wherein the adjuvant is selected from the group consisting of CpGs, M59, IFA (incomplete Freund's adjuvant), complete Freund's adjuvant, alum, bile salts, vitamins and attenuated toxins.

15. The vaccine composition according to claim 14, wherein the attenuated toxins are selected from pertussis and cholera.

16. The vaccine composition according to claim 11 for use in a method of contraception or for controlling fertility or heat in an animal.

17. The vaccine composition according to claim 11 wherein the animal is a human, a domestic animal, a wild animal, livestock or a fish.

18. The vaccine composition according to claim 11 which is administered orally, nasally, sub-cutaneously or trans-cutaneously to the animal.

* * * * *

SEQUENCE LISTING

```
<160> NUMBER OF SEQ ID NOS: 6

<210> SEQ ID NO 1
```

```
<211> LENGTH: 10
<212> TYPE: PRT
<213> ORGANISM: Artificial Sequence
<220> FEATURE:
<223> OTHER INFORMATION: Synthetic Construct
<220> FEATURE:
<223> OTHER INFORMATION: A retro-inverso gonadotropin release hormone
      peptide

<400> SEQUENCE: 1

Gly Pro Arg Leu Gly Tyr Ser Trp His Glu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct
<220> FEATURE:
<223> OTHER INFORMATION: A retro-inverso gonadotropin release hormone
      peptide

<400> SEQUENCE: 2

Gly Pro Arg Leu Gly Tyr Ser Trp His Glu Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10
<223> OTHER INFORMATION: Xaa = Any Amino Acid

<400> SEQUENCE: 3

Gly Pro Arg Leu Gly Tyr Ser Trp His Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10
<223> OTHER INFORMATION: Xaa = Glu, Gln, Pro, or Gly

<400> SEQUENCE: 4

Gly Pro Arg Leu Gly Tyr Ser Trp His Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10
<223> OTHER INFORMATION: Xaa = Glu or Gln

<400> SEQUENCE: 5

Gly Pro Arg Leu Gly Tyr Ser Trp His Xaa
```

-continued

```
                1               5                         10
<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Val Arg Thr Val Glu Asp Gly Glu Cys
  1               5
```